United States Patent
Kolonia et al.

(10) Patent No.: US 9,850,058 B2
(45) Date of Patent: Dec. 26, 2017

(54) TELESCOPING SYRINGE WITH ONE-WAY VALVE

(71) Applicant: New Product Development Concepts LLC, Phillipsburg, NJ (US)

(72) Inventors: Robert A. Kolonia, Milford, NJ (US); Brian J. Kolonia, Bath, PA (US)

(73) Assignee: New Product Development Concepts LLC, Phillipsburg, NJ (US)

( * ) Notice: Subject to any disclaimer, the term of this patent is extended or adjusted under 35 U.S.C. 154(b) by 0 days.

(21) Appl. No.: 15/504,678

(22) PCT Filed: Aug. 15, 2016

(86) PCT No.: PCT/US2016/046958
§ 371 (c)(1),
(2) Date: Feb. 17, 2017

(87) PCT Pub. No.: WO2017/044252
PCT Pub. Date: Mar. 16, 2017

(65) Prior Publication Data
US 2017/0275080 A1    Sep. 28, 2017

Related U.S. Application Data

(60) Provisional application No. 62/217,352, filed on Sep. 11, 2015.

(51) Int. Cl.
*A61M 5/315* (2006.01)
*B65D 83/00* (2006.01)
(Continued)

(52) U.S. Cl.
CPC ........... *B65D 83/0022* (2013.01); *A61M 5/31* (2013.01); *A61M 5/3145* (2013.01);
(Continued)

(58) Field of Classification Search
CPC ......... B65D 83/0022; B05C 17/00593; A61M 5/315; A61M 5/31513; A61M 5/31; A61M 5/3145; A61M 2005/3128; A61M 39/24
See application file for complete search history.

(56) References Cited

U.S. PATENT DOCUMENTS 1,557,836 A    10/1925  Hein
2,869,543 A *  1/1959  Ratcliff ................... A61M 5/19
                                                                    604/90
(Continued)

FOREIGN PATENT DOCUMENTS

CN    102861369 B    4/2015
EP      0242956 A1   10/1987
(Continued)

*Primary Examiner* — Nicholas J Weiss
(74) *Attorney, Agent, or Firm* — Michael Crilly, Esquire

(57) ABSTRACT

A telescoping syringe suitable for use with medications and other ejectable or injectable fluids is presented. The syringe includes a plunger, a barrel, and a valve. The plunger is extendible from and retractable into the barrel. The plunger defines a first reservoir. The barrel defines a second reservoir as the plunger is extended from the barrel. The valve is disposed at one end of the plunger adjacent to a nipple extending from the barrel. A first sealing interface is formed by the valve and a distal wall along the barrel adjacent to the nipple. A second sealing interface is formed by an annular flange along the one-way valve and an annular groove along the plunger. A third sealing interface is formed by the valve and a circumferential end along the plunger. The sealing interfaces are closed prior to extension of the plunger from the barrel thereby preventing a gas from entering and a fluid from existing the first reservoir. The sealing interfaces are open when the plunger is extended from the barrel so that the gas enters the first reservoir via an inlet(s) along the annular groove and fluid is communicated into the second reservoir
(Continued)

via an outlet(s) along the valve. The second and third sealing interfaces are closed when the plunger is retracted into the barrel thereby allowing fluid to exit the second reservoir via the nipple.

19 Claims, 14 Drawing Sheets

(51) Int. Cl.
  *A61M 5/31* (2006.01)
  *B05C 17/005* (2006.01)
(52) U.S. Cl.
  CPC ... *A61M 5/31513* (2013.01); *B05C 17/00593* (2013.01); *A61M 2005/3128* (2013.01)

(56) References Cited

U.S. PATENT DOCUMENTS

| | | | |
|---|---|---|---|
| 2,869,544 A | 1/1959 | Ratcliff et al. | |
| 3,076,456 A | 2/1963 | Hunt, Sr. | |
| 3,464,412 A | 9/1969 | Schwartz | |
| 3,685,514 A | 8/1972 | Cheney | |
| 3,699,961 A | 10/1972 | Szpur | |
| 4,153,186 A | 5/1979 | Nye | |
| 4,934,379 A * | 6/1990 | Marzolf | A61B 5/15003 600/578 |
| 5,338,294 A | 8/1994 | Blake, III | |
| 5,695,465 A | 12/1997 | Zhu | |
| 5,785,682 A | 7/1998 | Grabenkort | |
| 5,785,683 A | 7/1998 | Szapiro et al. | |
| 6,080,131 A | 6/2000 | Van Der Meyden et al. | |
| 6,193,695 B1 | 2/2001 | Rippstein, Jr. | |
| 6,508,792 B2 | 1/2003 | Szames et al. | |
| 6,602,223 B2 | 8/2003 | Szapiro et al. | |
| 8,632,519 B2 | 1/2014 | Lum et al. | |
| 9,408,971 B2 * | 8/2016 | Carlyon | A61M 5/28 |
| 9,586,008 B2 * | 3/2017 | Shetty | A61M 5/2448 |
| 2002/0087122 A1 | 7/2002 | Sogaro | |
| 2003/0040701 A1 | 2/2003 | Dalmose | |
| 2015/0025454 A1 | 1/2015 | Wetzel et al. | |
| 2015/0025455 A1 | 1/2015 | Shetty et al. | |
| 2015/0025456 A1 | 1/2015 | Shetty et al. | |

FOREIGN PATENT DOCUMENTS

| | | |
|---|---|---|
| WO | 8809679 A1 | 12/1988 |
| WO | 9917820 A1 | 4/1999 |
| WO | 2008076150 A2 | 6/2008 |

\* cited by examiner

TELESCOPING SYRINGE WITH ONE-WAY VALVE

CROSS REFERENCE TO RELATED APPLICATIONS

This application is a National Phase of PCT Application No. PCT/US2016/046958 filed Aug. 15, 2016 which further claims priority from U.S. Provisional Application No. 62/217,352 filed Sep. 11, 2015, each entitled Telescoping Syringe with One-Way Valve. The subject matters of the prior applications are incorporated in their entirety herein by reference thereto.

FEDERALLY SPONSORED RESEARCH AND DEVELOPMENT

None.

BACKGROUND OF THE INVENTION

1. Field of the Invention

The invention generally relates to a telescoping syringe with a plunger extendible from and retractable into a barrel and more particularly is concerned, for example, with an improved valve mechanism between reservoirs within a syringe. Specifically, the valve is extendible from and retractable onto one end of the plunger. The valve prevents leakage of a fluid from the syringe prior to extension of the plunger from the barrel. The valve also permits transfer of a fluid from a first reservoir within the plunger into a second reservoir within the barrel during extension of the plunger from the barrel. The valve further facilitates ejection of a fluid from the second reservoir during retraction of the plunger into the barrel.

2. Background

A variety of telescoping syringes are known within the art. Conventional syringes are often used in connection with a vial containing a fluid, typically a medication or other injectable or ejectable fluid, whereby the user draws fluid into the syringe. It is common for some syringes to be packaged as prefilled devices, whereby a syringe is sold to the end user prefilled with fluid already residing within the syringe. Prefilled syringes are beneficial in that such devices eliminate one or more steps required for proper use thereby reducing the cost of use and in that such devices control the quantity of fluid delivered thereby reducing errors associated with use.

However, prefilled syringes and packaging therefore tend to be bulky because the barrel is filled with fluid requiring the plunger to extend from the barrel. The elongated nature of prefilled syringes and packaging therefore increases non-use costs associated with shipping and storage by virtue of the greater volume occupied by the prefilled device.

Medical applications of prefilled syringes are particularly problematic in that the fluid contained within the syringe often must be safeguarded from theft via storage within a locked cabinet or the like. The space available for secured storage is often limited and costly, thus creating a need for prefilled syringes to have a smaller footprint with and without packaging.

It is further understood that the related arts do not provide a mechanism that reliably and simply facilitates proper function of a telescoping syringe. For example, known telescoping syringes are mechanically complex in design and use, functionally unreliable, difficult to manufacture, and/or costly. Furthermore, known telescoping syringes are prone to leakage and unable to prevent or minimize air surrounding the syringe from entering a second or ejection reservoir as fluid is transferred from a first or storage reservoir to the ejection reservoir.

For at least the reasons discussed above, the benefits and advantages of telescoping-type syringes have yet to be completely realized.

Accordingly, what is required is a telescoping syringe that is mechanically simple in design and use, functionally reliable, easily manufactured, and less costly to package, ship, store and use.

SUMMARY OF THE INVENTION

An object of the invention is to provide a telescoping syringe that is mechanically simple in design and use, functionally reliable, easily manufactured, and less costly to package, ship, store and use.

In accordance with embodiments of the invention, the telescoping syringe includes a barrel, a plunger, and a one-way valve. The plunger is extendible from and retractable into the barrel. The plunger defines a first reservoir. The barrel defines a second reservoir as the plunger is extended from the barrel. The one-way valve is disposed at one end of the plunger adjacent to a nipple extending from the barrel. A first sealing interface is provided by the one-way valve and a distal wall along the barrel adjacent to the nipple. A second sealing interface is provided by an annular flange along the one-way valve and an annular groove along the plunger. A third sealing interface is provided by the one-way valve and a circumferential end of the plunger. The first, second, and third sealing interfaces are closed prior to extension of the plunger from the barrel thereby preventing a gas from entering and a fluid from existing the first reservoir. The first, second, and third sealing interfaces are open when the plunger is extended from the barrel so that the gas enters the first reservoir via an inlet(s) along the annular groove and the fluid is communicated into the second reservoir via an outlet(s) along the one-way valve. The second and third sealing interfaces are closed when the plunger is retracted into the barrel thereby allowing the fluid to exit the second reservoir via the nipple.

In accordance with other embodiments of the invention, the first sealing interface is closed when the one-way valve contacts the distal wall and the first sealing interface is open when the one-way valve is separated from the distal wall.

In accordance with other embodiments of the invention, the annular flange slidingly engages the annular groove so that the second sealing interface is closed when the annular flange completely covers the inlet(s) along the annular groove and the second sealing interface is open when the annular flange does not completely cover the inlet(s).

In accordance with other embodiments of the invention, the second sealing interface extends along and includes a proximal shoulder along the plunger and an annular extension along the one-way valve to the extent which contact is permitted between the proximal shoulder and the annular extension. The second sealing interface is closed when the annular extension contacts the proximal shoulder and is open when the annular extension is pulled away from and no longer contacts the proximal shoulder.

In accordance with other embodiments of the invention, the third sealing interface is closed when the circumferential end contacts the one-way valve so as to overlay and cover the outlet(s) along the one-way valve and the third sealing interface is open when the circumferential end is separated from the one-way valve.

In accordance with other embodiments of the invention, the telescoping syringe further includes a break-away valve that engages the barrel adjacent to the nipple thereby defining a fourth sealing interface. The break-away valve is attached to the one-way valve and the fourth sealing interface is closed prior to extension of the plunger from the barrel thereby preventing the gas from entering the barrel. The break-away valve is detached from the one-way valve and the fourth sealing interface is closed during extension of the plunger from the barrel thereby forming a lower pressure within the second reservoir, which may also include a like-vacuum condition, than the pressure within the first reservoir which facilitates transfer of the fluid from the first reservoir to the second reservoir. The break-away valve is detached from the one-way valve and the fourth sealing interface is open during retraction of the plunger into the barrel thereby allowing the fluid to exit the second reservoir via the nipple.

In accordance with other embodiments of the invention, the break-away valve includes a stem interposed between the one-way valve and a plug. The plug is attached to the one-way valve via the stem. The stem permits the plug to detach from the one-way valve when the plunger is extended from the barrel.

In accordance with other embodiments of the invention, the telescoping syringe further includes a diaphragm adjacent to the nipple. The diaphragm is interposed between the plug and the one-way valve.

In accordance with other embodiments of the invention, the stem traverses an opening through the diaphragm and the stem is attached to the one-way valve and the plug before extension of the plunger from then barrel.

In accordance with other embodiments of the invention, the fourth sealing interface is closed when the plug contacts the diaphragm and the fourth sealing interface is open when the plug is separated from the diaphragm.

In accordance with other embodiments of the invention, the telescoping syringe further includes a stop(s) disposed along an opening through the nipple. The stop(s) permits the fluid to traverse and exit the nipple and prevents the plug from exiting the nipple.

In accordance with other embodiments of the invention, the telescoping syringe further includes a filter element disposed along the telescoping syringe. Gas passes through the filter element prior to entering the inlet(s).

In accordance with other embodiments of the invention, the filter element is interposed between a first side wall of the plunger and a second side wall of the barrel. Gas traverses a gap between the first side wall and the second side wall.

In accordance with other embodiments of the invention, the filter element is a HEPA filter.

In accordance with other embodiments of the invention, the telescoping syringe further includes a biasing mechanism which permits the one-way valve to extend from the plunger when extended from the barrel and then causes the one-way valve to retract onto the plunger.

In accordance with other embodiments of the invention, the biasing mechanism causes the one-way valve to retract onto the plunger after at least some fluid is transferred from the first reservoir to the second reservoir.

In accordance with other embodiments of the invention, the biasing mechanism causes the one-way valve to retract onto the plunger after the plunger extends from the barrel.

In accordance with other embodiments of the invention, the biasing mechanism is deformable and resilient.

In accordance with other embodiments of the invention, the biasing mechanism includes an elastic annular flange along the one-way valve which interacts with a shoulder along the plunger.

As described herein, the telescoping syringe includes a barrel and a plunger. The plunger further includes a one-way valve at a distal end thereof and a first reservoir therein. The plunger is disposed within the barrel so that the plunger is extendable from and retractable into the barrel. The valve prevents gas from leaking into the first reservoir and fluid from leaking out of the first reservoir prior to use of the syringe. The valve simultaneously permits the gas to fill the first reservoir and the fluid to exit the first reservoir during extension of the plunger from the barrel. The valve also prevents the gas from exiting the first reservoir and the fluid from reentering the first reservoir during retraction of the plunger into the barrel.

A user pulls on one end of the plunger to extend or telescope the plunger from the barrel. The one-way valve permits the fluid within the first reservoir to pass through the valve and to fill a second reservoir within the barrel. The second reservoir is formed during extension of the plunger from the barrel so that the volume of the second reservoir is approximately equal to the volume vacated by the plunger. Gas fills the plunger as the fluid moves from the plunger into the barrel. The user then depresses the plunger causing the plunger to retract into the barrel so that the fluid now residing in the second reservoir exits the syringe via a nipple at the distal end of the syringe.

The valve is attached to the plunger in an extendable/retractable arrangement. The valve includes a substantially circular-shaped barrier or wall and an annular extension therefrom, the latter attached to and extending from the outer circumference of the barrier. The barrier further includes one or more outlets positioned to align with the circumferential end of a side wall along the plunger.

The plunger is disposed within the barrel prior to use of the syringe so that the one-way valve is adjacent to the nipple part of the syringe. The valve contacts the barrel adjacent to the nipple along the barrel thereby sealing the front end of the syringe to prevent leakage of atmosphere surrounding the syringe into and fluid within the syringe from the syringe. The valve is slidably seated onto the circumferential end of the plunger so as to align with and cover the outlets, thereby closing and sealing the outlets, when the valve is seated onto the plunger. This arrangement prevents the gas from entering and fluid from exiting the plunger prior to use. The annular extension also overlays and covers inlets along the side wall of the plunger, thereby closing and sealing the inlets, when the valve is retracted onto the plunger. This arrangement prevents the gas from exiting from and fluid from reentering the first reservoir.

When the plunger is extended from the barrel, a lower pressure is formed within the barrel adjacent to the nipple causing the valve to extend from the plunger thereby separating the circumferential end from the outlets and allowing fluid within the first reservoir, residing within the plunger, to flow into the second reservoir, residing within the barrel, via the outlets. Extension of the valve also exposes inlets along the side wall of the plunger thereby allowing a gas surrounding the syringe to enter the first reservoir as fluid in transferred from the first reservoir into the second reservoir. The plunger is extended so that at least a portion of the fluid is transferred from the first reservoir to the second reservoir.

Formation of the lower pressure within the second reservoir is possible when the flow of gas into the second reservoir is restricted during extraction of the plunger from the barrel. Gas flow into the second reservoir via the nipple is avoided by either a removable cap attached to the nipple or a valve-mechanism adjacent to the nipple. Gas flow into the second reservoir via a gap or space between the side walls of the plunger and barrel is also avoided by a seal between the inner diameter of the barrel and outer diameter of the valve. The valve may include one or more concave and/or convex ridges that extend therefrom and slidingly contact the inner diameter of the barrel thereby defining a slidable seal.

When the plunger is retracted into the barrel, the valve retracts onto the plunger closing both inlets and outlets so as to prevent fluid from reentering and gas from exiting the first reservoir. The fluid within the second reservoir along the barrel flows into and through the nipple as the plunger is retracted into the barrel. The plunger is retracted so that at least a substantial portion of the fluid is ejected from the second reservoir.

In some applications, the plunger may be partially extended from the barrel during use so that less than all fluid is transferred from the first reservoir into the second reservoir. The plunger is then retracted into the barrel so that less than all fluid contained within the syringe is ejected from the second reservoir. The extension and retractions steps may be repeated until all fluid is expelled from the syringe. This functionality facilitates a multi-use capability by the invention. The syringe may include indicia or other markings that permit a user to transfer the desired amount from the first reservoir to the second reservoir for each transfer/ejection cycle.

A valve-like seal may be beneficial in some embodiments when a cap is not secured to the nipple prior to extension of the plunger. An optional break-away valve may be attached to the one-way valve to achieve a lower pressure region adjacent to the nipple and the one-way valve prior to extension of the plunger. The break-away valve may seal the nipple before and during extension of the plunger. The break-away valve may also seal the nipple as fluid is transferred from the first reservoir to the second reservoir. When the plunger is retracted, the break-away valve may traverse a portion of the nipple so as to engage stops within the nipple which permit the fluid to exit the syringe but not the break-away valve.

An optional filter may be advantageous in some embodiments along the interface between the side walls of the plunger and the barrel. A pocket is provided along the side wall of the barrel, preferably adjacent to the proximal end of the syringe. The pocket is sized so that a filter element may be secured between the side walls without impeding the sliding motion required between the barrel and the plunger for proper function of the syringe. The filter element communicates with a gap between the side walls so as to permit the gas to pass through the filter and then traverse the gap in the direction of the valve. The filtered gas enters the first reservoir via the inlets thereby replacing the fluid transferred to the second reservoir so as to avoid a vacuum within the first reservoir.

In other embodiments, it may be advantageous for the valve to include a biasing mechanism that retracts and reseats the valve onto the plunger. The biasing mechanism may be a device that is functionally similar to a spring. In preferred embodiments, the biasing mechanism is deformable, yet resilient so as to allow the biasing mechanism to elastically deform during extension of the plunger and elastically recovers its original shape after the plunger is extended to the desired length and/or the desired quantity of liquid is transferred from the first reservoir to the second reservoir. One non-limiting example of a biasing mechanism is an elastic annular flange along the valve which interacts with a shoulder along the plunger.

In its simplest form, the invention may be comprised of three components, namely, a plunger, a barrel, and a one-way valve, each composed of a plastic molded via injection molding techniques understood in the art. However, other materials and manufacturing methods are likewise suitable to the present invention. The invention is readily manufacturable, user friendly, functionally reliable, and a cost effective alternative to the various telescoping syringe designs currently known within the art. The invention provides a compact form by virtue of the plunger retracted into the barrel prior to use which in turn reduces packaging, shipping, and storage costs. The retracted arrangement of the plunger prior to use also avoids accidental ejection of fluid from the syringe when the syringe is inadvertently dropped prior to extension of the plunger from the barrel. The invention is compatible with and applicable to injectable and ejectable fluids suitable to prefilled syringes sold to users as a self-contained and fully-functional product. The valve mechanism allows end users to selectively dispense less than all fluid contained within the plunger thereby facilitating multi-use capability.

The above and other objectives, features, and advantages of the preferred embodiments of the invention will become apparent from the following description read in connection with the accompanying drawings, in which like reference numerals designate the same or similar elements.

BRIEF DESCRIPTION OF THE DRAWINGS

Additional aspects, features, and advantages of the invention will be understood and will become more readily apparent when the invention is considered in the light of the following description made in conjunction with the accompanying drawings.

DETAILED DESCRIPTION OF THE INVENTION

Figure 1:
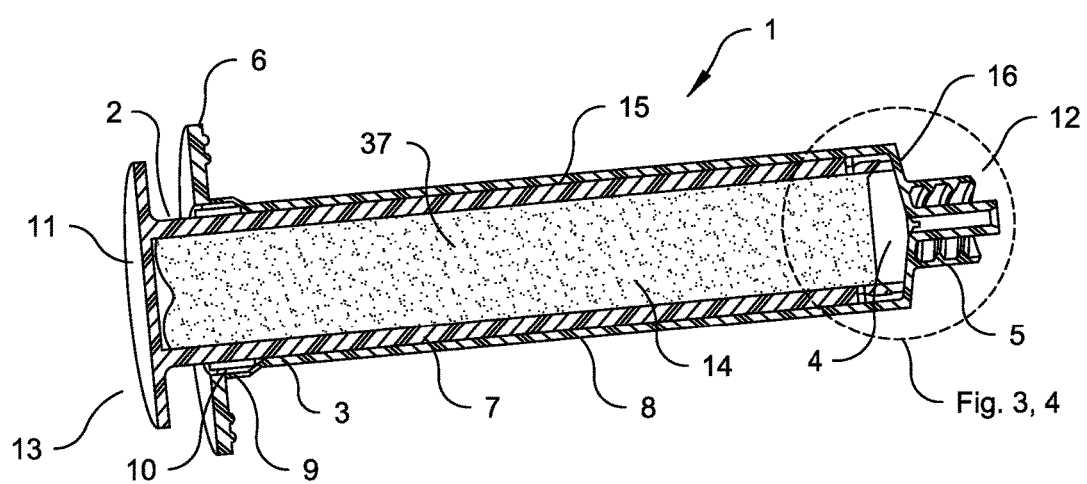
FIG. 1 is a perspective cross-sectional view illustrating a telescoping syringe including a barrel, a plunger, and a valve prior to extension of the plunger from the barrel in accordance with an embodiment of the invention.

Reference will now be made in detail to several embodiments of the invention that are illustrated in the accompanying drawings. Wherever possible, same or similar reference numerals are used in the drawings and the description to refer to the same or like parts. The drawings are in simplified form and are not to precise scale.

While features of various embodiments are separately described herein, it is understood that such features may be combinable to form other additional embodiments.

Components described herein are manufactured via methods, processes, and techniques understood in the art, including, but not limited to, machining, molding, forming, and three-dimensional printing. Components may be composed of any suitable material including, but not limited to, injection moldable thermoplastics.

Referring now to FIG. 1, the syringe 1 includes a plunger 2, a barrel 3, and a valve 4. The plunger 2 is a tube-shaped element with a cavity therein defined by a substantially cylindrical-shaped side wall 7 with a substantially planar-shaped proximal wall 11 at first end thereof and an opening at a second end. The barrel 3 is a tube-shaped element with a cavity therein defined by a substantially cylindrical-shaped side wall 8 with a distal wall 16 at one end thereof and an opening at a second end. The inner diameter of the barrel 3 and outer diameter of the plunger 2 are sized so as to allow a slidable engagement therebetween. This arrangement permits insertion of the plunger 2 into the barrel 3 and extension of the plunger 2 from the barrel 3. The proximal wall 11 is positioned at the proximal end 13 of the syringe 1. A flange 6 extends from the barrel 3 adjacent to the proximal end 13. The flange 6 and proximal wall 11 are shaped to allow a user to pull and extend the plunger 2 from the barrel 3 and to push and retract the plunger 2 into the barrel 3. The distal wall 16 is positioned adjacent to the distal end 12 of the syringe 1. A nipple 5 extends from the distal wall 16.

Referring again to FIG. 1, the valve 4 is secured to the second end of the side wall 7 along the plunger 2 adjacent to the distal wall 16. The valve 4, side wall 7, and proximal wall 11 define a cavity referred to as the first reservoir 14. The first reservoir 14 is initially sealed as discussed herein to contain a fluid 37. The volume occupied by the plunger 2 within the barrel 3 further generally defines a second reservoir 15. The actual volume of the second reservoir 15 is defined by the volume bounded by the side wall 8, distal wall 16, and valve 4. The second reservoir 15 has no or minimal actual volume when the plunger 2 is retracted into the barrel 3. As the plunger 2 is extended from the barrel 3, the actual volume of the second reservoir 15 increases proportional to the length of the plunger 2 extended from the barrel 3. In preferred embodiment, the volume of the second reservoir 15 should be substantially comparable to the volume of the first reservoir 14 when the plunger 2 is substantially extended from the barrel 3.

Figure 2:
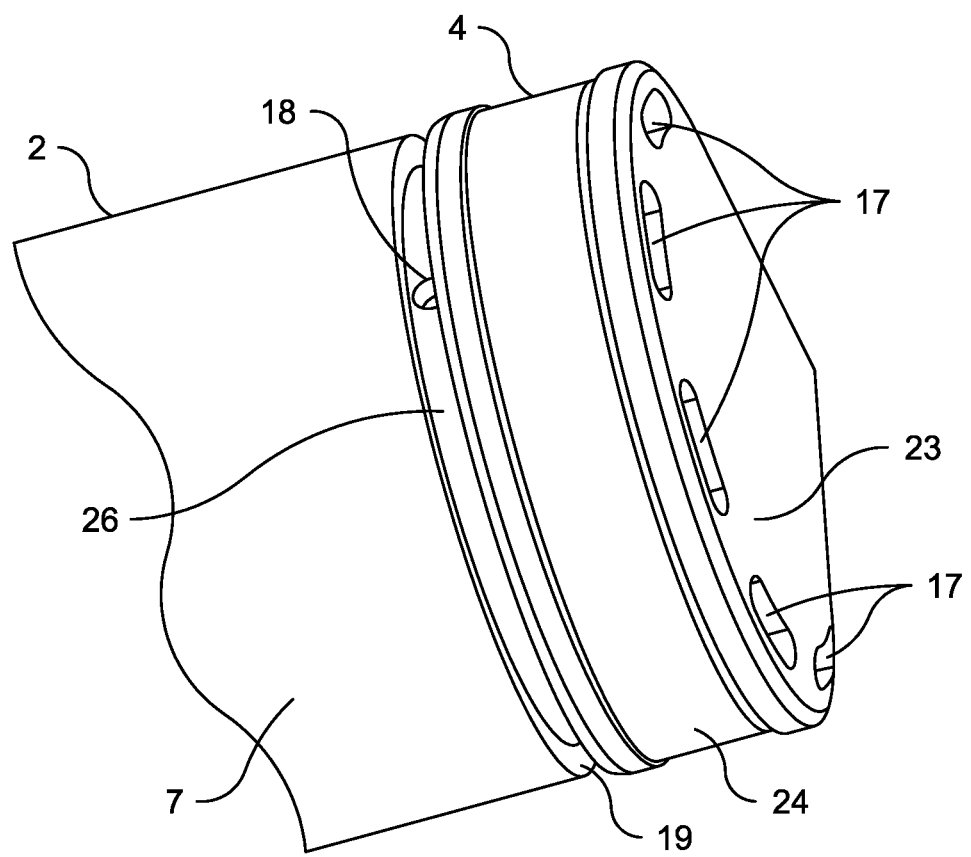
FIG. 2 is an enlarged perspective view illustrating a valve extendible from and retractable onto one end of a plunger whereby the valve includes at least one outlet and the plunger includes at least one inlet in accordance with an embodiment of the invention.
Figure 3:
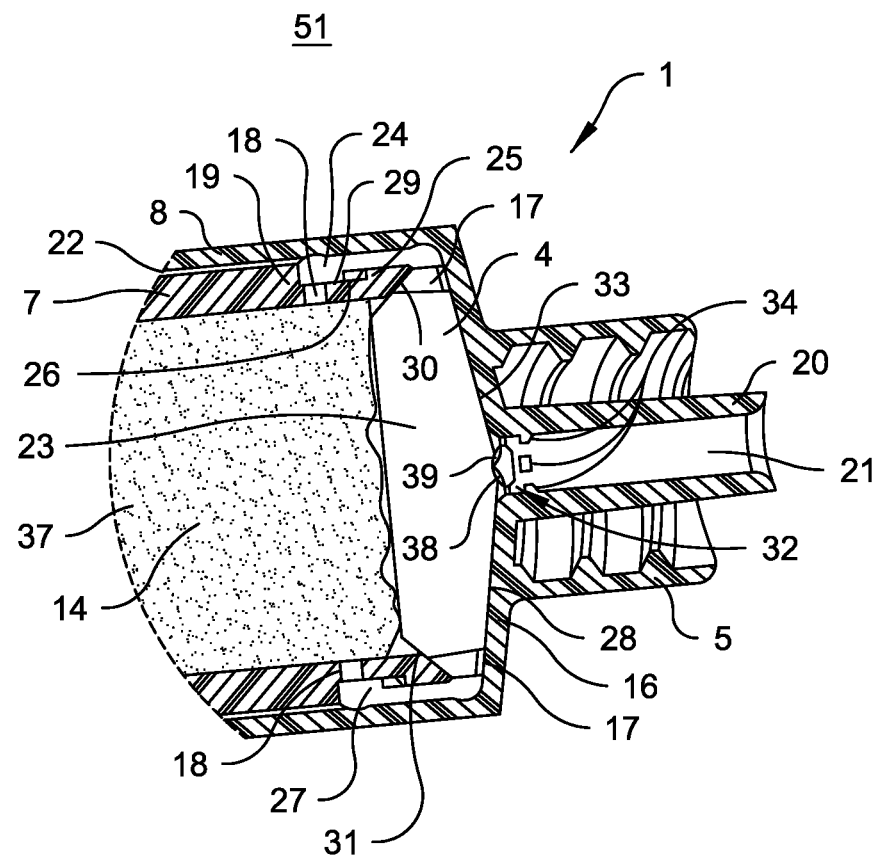
FIG. 3 is an enlarged cross-sectional view illustrating a valve prior to extension of a plunger from a barrel whereby the valve is disposed in a closed configuration to prevent escape of a fluid from a first reservoir within the plunger in accordance with an embodiment of the invention.
Figure 4:
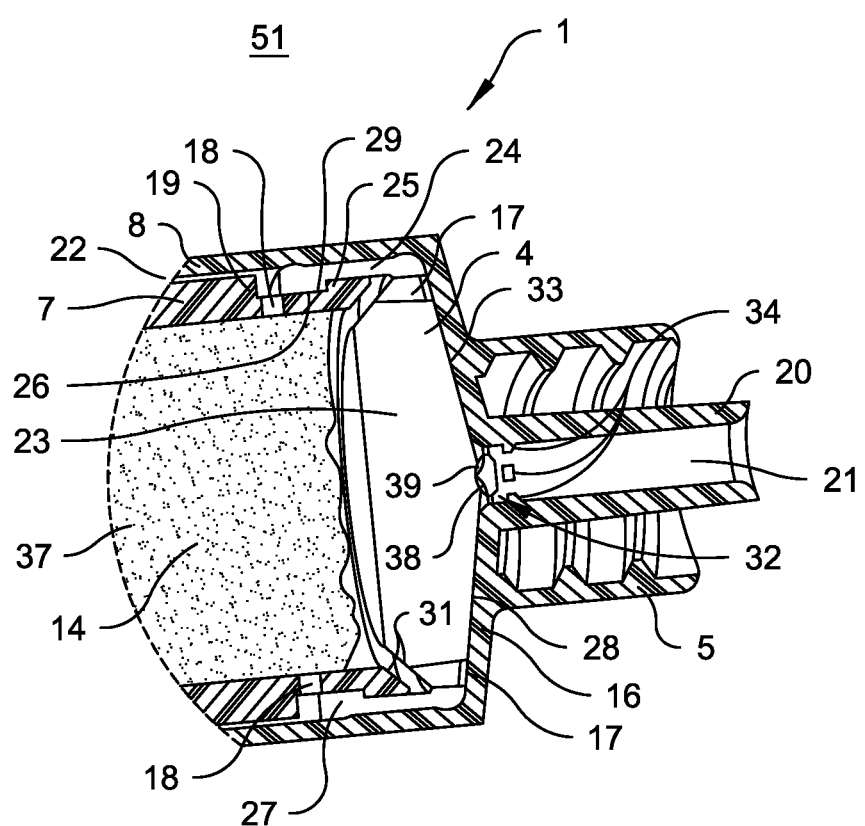
FIG. 4 is an enlarged cross-sectional view illustrating a valve after initial extension of a plunger from a barrel whereby the valve is extended from the plunger and disposed in an open configuration to permit a gas to enter a first reservoir and to permit transfer of a fluid from the first reservoir within the plunger to a second reservoir within the barrel in accordance with an embodiment of the invention.

Referring now to FIGS. 2-4, the valve 4 includes a disk-shaped barrier 23 and an annular extension 24. The annular extension 24 is a ring-shaped element that extends from the barrier 23 adjacent to the outer circumference of the barrier 23. An annular flange 27 extends radially inward from the annular extension 24. The valve 4 further includes at least one outlet 17 defined by an opening that traverses the thickness of the barrier 23. The outlets 17 are positioned along the barrier 23 so as to align with the circumferential end 30 of the side wall 7 along the plunger 2. The outlets 17 and side wall 7 are dimensioned so that contact between the circumferential end 30 and the barrier 23 ensures the end surface of the side wall 7 completely covers and thereby seals the outlets 17 when the valve 4 is retracted onto the plunger 2.

Referring again to FIGS. 2-4, the side wall 7 further includes an annular groove 26 bounded by a proximal shoulder 19 and a distal shoulder 25. At least one inlet 18 defined by an opening traversing the thickness of the side wall 7 is provided along the annular groove 26. The inlets 18 communicate with a gap 22 or other comparable opening along or between the side walls 7, 8 to permit a gas 51 adjacent to the syringe 1 to enter the first reservoir 14 as fluid 37 exits therefrom.

Referring again to FIGS. 2-4, the valve 4 is seated onto the side wall 7 so that the annular flange 27 engages the annular groove 26. The dimensions of the annular flange 27 and annular groove 26 ensure a slidable engagement between the valve 4 and the plunger 2. This arrangement permits the valve 4 to extend from and retract onto plunger 2 within the limits imposed by the proximal shoulder 19 and the distal shoulder 25. The inlets 18, annular groove 26, annular flange 27, proximal shoulder 19, and distal shoulder 25 are arranged so that the annular flange 27 overlays and seals the inlets 18 when the annular flange 27 is biased toward the proximal shoulder 19 and the annular flange 27 does not seal the inlets 18 when the annular flange 27 is biased toward the distal shoulder 25. In preferred embodiments, the outlets 17, circumferential end 30, annular groove 26, annular flange 27, proximal shoulder 19, and distal shoulder 25 are arranged so that the circumferential end 30 overlays and seals the outlets 17 when the annular flange 27 contacts the proximal shoulder 19, as illustrated in FIG. 3, and the circumferential end 30 neither overlays nor seals the outlets 17 when the annular flange 27 contacts the distal shoulder 25, as illustrate in FIG. 4.

The nipple 5 is attached to and extends from the distal wall 16. The nipple 5 includes a port 20 with an opening 21 therethrough. The opening 21 provides a pathway enabling fluid 37 within the second reservoir 15 to exit the syringe 1. The nipple 5 and port 20 may include features or elements that enable attachment of a cap and/or needle to the syringe 1.

Referring again to FIGS. 2-4, the valve 4 provides sealing critical to function of the syringe 1. A first sealing interface 28 is formed by the valve 4 and the distal wall 16. In preferred embodiments, the outer surface of the barrier 23 along the valve 4 contacts the inner surface of the distal wall 16 to form a contact seal that prevents fluid 37 from reaching the nipple 5 prior to extension of the plunger 2. The first sealing interface 28 is closed when the barrier 23 contacts the distal wall 16 and open when the barrier 23 is separated from the distal wall 16. A second sealing interface 29 is formed by the valve 4 and the surface of the side wall 7. In preferred embodiments, the inner circumferential surface of the annular flange 27 slidably contacts the outer circumferential surface of the annular groove 26 so as to overlay the inlets 18 prior to extension of the plunger 2 thereby preventing gas 51 from reaching the fluid 37 and during retraction of the plunger 2 to prevent gas 51 from exiting and fluid 37 from reentering the first reservoir 14. The second sealing interface 29 is closed when the annular flange 27 completely overlays the inlets 18 and open when the annular flange 27 does not completely overlay the inlets 18. A third sealing interface 31 is formed by the valve 4 and the circumferential end 30 of the side wall 7. In preferred embodiments, the circumferential end 30 should contact the barrier 23 so as to overlay the outlets 17 prior to extension of the plunger 2 to prevent fluid 37 from reaching the nipple 5 and during retraction of the plunger 2 to prevent fluid 37 from reentering the first reservoir 14. The third sealing interface 31 is closed when the circumferential end 30 contacts the inside surface of the barrier 23 and open when the circumferential end 30 is separated from the barrier 23.

In some embodiments, the second sealing interface 29 may extend along and include a surface along the proximal shoulder 19 and a surface along the annular extension 24 to the extent that contact is permitted between the surfaces. The second sealing interface 29 along the proximal shoulder 19 is closed when the annular extension 24 contacts the proximal shoulder 19 and is open when the annular extension 24 is pulled away from and no longer contacts the proximal shoulder 19.

Figure 5:
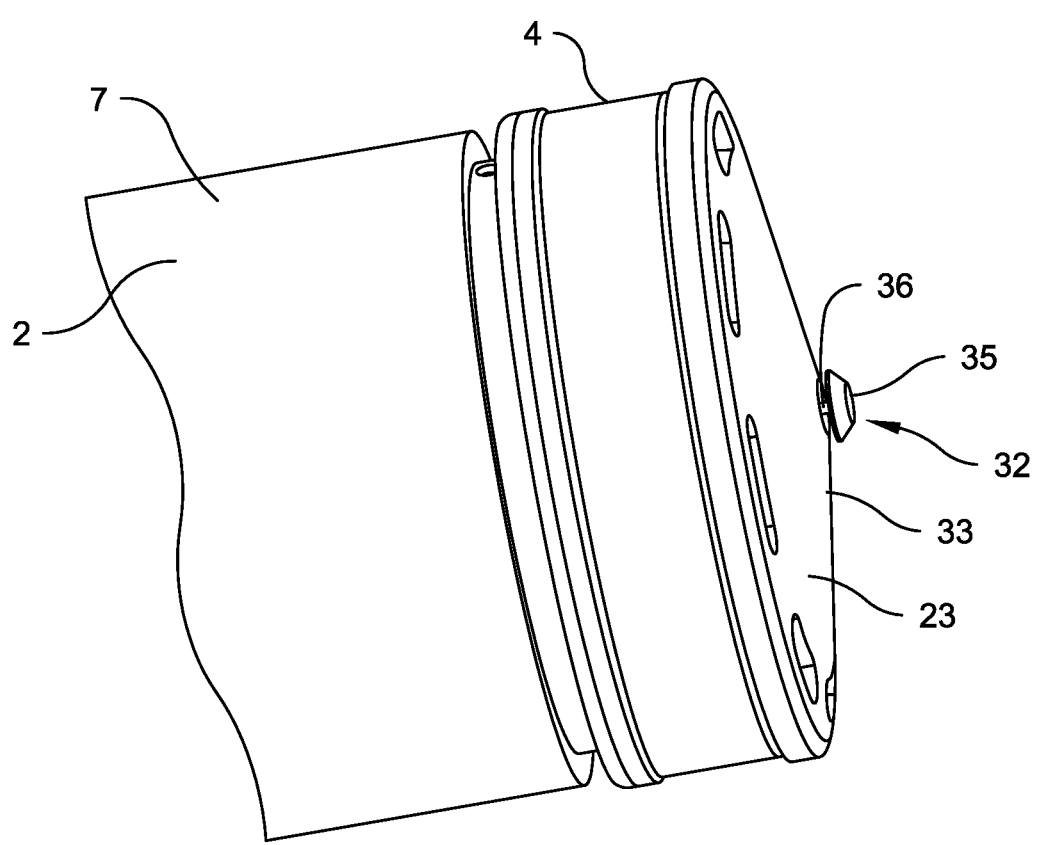
FIG. 5 is an enlarged perspective view illustrating a valve extendible from and retractable onto one end of a plunger whereby the valve is extended from the plunger, the valve includes at least one outlet, the plunger includes at least one inlet, and an optional break-away valve is attached to the plunger in accordance with an embodiment of the invention.

Referring now to FIGS. 3-5, an optional break-away valve 32 may be provided along the outer surface 33 of the barrier 23 so as to align with the nipple 5. The break-away valve 32 may include a plug 35 and a stem 36. The plug 35 is generally shaped, dimensioned, and positioned so as to engage the port 20 and seal the opening 21. This arrangement provides a fourth sealing interface 39 between valve 4 and nipple 5 adjacent to the opening 21. The stem 36 is an element which secures the plug 35 to the valve 4, yet remains separable or breakable when extension forces are communicated to the valve 4 via the plunger 2. In one non-limiting example, the stem 36, plug 35, and valve 4 could be molded as a single component. In another non-limiting example, the stem 36 and plug 35 could be separately molded from the valve 4 and either mechanically or adhesively fastened thereto. Regardless of the construction and assembly approaches for the break-away valve 32, the stem 36 should ensure attachment of the plug 35 to the valve 4 prior to extension and should mechanically break or separate from the plug 35 or the valve 4 when the plunger 2 is extended from the barrel 3.

Referring again to FIGS. 3-5, one or more optional stops 34 may be positioned within the nipple 5 when a break-away valve 32 is attached to the valve 4. The stops 34 are nub-like elements or the like separately spaced about the port 20 so as to extend inward along the opening 21. The stops 34 are dimensioned so as to minimize interaction with fluid 37 traversing the nipple 5. However, the stops 34 are positioned and dimensioned so as to prevent the plug 35 and the stem 36 from completely traversing the port 20 after separation from the valve 4. This feature ensures proper function of the syringe 1 by preventing ejection of the plug 35 and the stem 36 from the syringe 1.

Referring again to FIGS. 3-5, an optional diaphragm 38 may be provided along the port 20 immediately adjacent to the valve 4. The diaphragm 38 could be a thin, flexible annular element which extends either from the port 20 so as to engage the plug 35 and/or the stem 36 or from the plug 35 and/or stem 36 so as to engage the port 20. The diaphragm 38 further seals the port 20 to insure the integrity of the fourth sealing interface 39, yet minimize obstructions that impede ejection of the fluid 37 from the syringe 1 when the fourth sealing interface 39 is open.

Referring again to FIGS. 3-5, the fourth sealing interface 39 may be beneficial when the syringe 1 does not include a cap or other means that support function of the valve 4. In preferred embodiments, the fourth sealing interface 39 is closed prior to and during extension of the plunger 2 from the barrel 3 to prevent the flow of gas 51 through the nipple 5 and open during retraction to permit ejection of the fluid 37 through the nipple 5. The fourth sealing interface 39 is closed when the plug 35 contacts the diaphragm 38 and open when the plug 35 is separated from the diaphragm 38.

Figure 6:
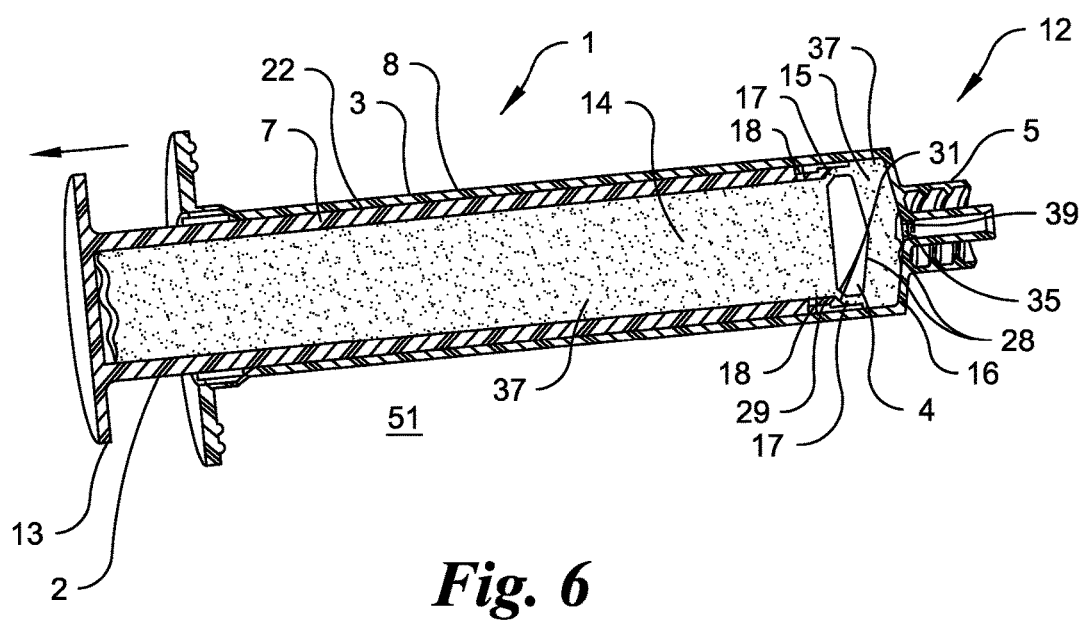
FIG. 6 is a perspective cross-sectional view illustrating flow of a fluid from a first reservoir through a valve into a second reservoir and location of an optional break-away valve after the valve is extended from the plunger and during extension of the plunger from a barrel of a telescoping syringe in accordance with an embodiment of the invention.

Referring now to FIG. 6, a syringe 1 is shown during extension of a plunger 2 from a barrel 3 whereby the side wall 7 along the plunger 2 moves toward the proximal end 13 and the side wall 8 along the barrel 3 remains fixed relative to the distal end 12. The plunger 2 is extended by pulling the plunger 2 away from the barrel 3 along the extension axis of the syringe 1. As the side wall 7 slides along the side wall 8, a lower pressure event is created between the plunger 2 and barrel 3 adjacent to the nipple 5 which temporarily fixes the valve 4 to the distal wall 16. After the valve 4 is fully extended from the side wall 8, the valve 4 then moves with the plunger 2 and away from the distal wall 16 thus providing the volume within the barrel 3 required to support the second reservoir 15. The result is an opening of the first, second, and third sealing interfaces 28, 29, 31. The optional fourth sealing interface 39 remains closed. When the first sealing interface 28 is opened, either a cap along the nipple 5 or the plug 35 prevents a gas 51 from entering the nipple 5 thereby maintaining the pressure conditions required to transfer fluid 37 from the first reservoir 14 to the second reservoir 15. When the second sealing interface 29 is open, the gas 51 surrounding the syringe 1, one non-limiting example being air, is drawn into the gap 22 and then traverses the valve 4 via the inlets 18 into the first reservoir 14. When the third sealing interface 31 is open, the fluid 37 traverses the valve 4 via the outlets 17 and enters the expanding second reservoir 15.

Figure 7:
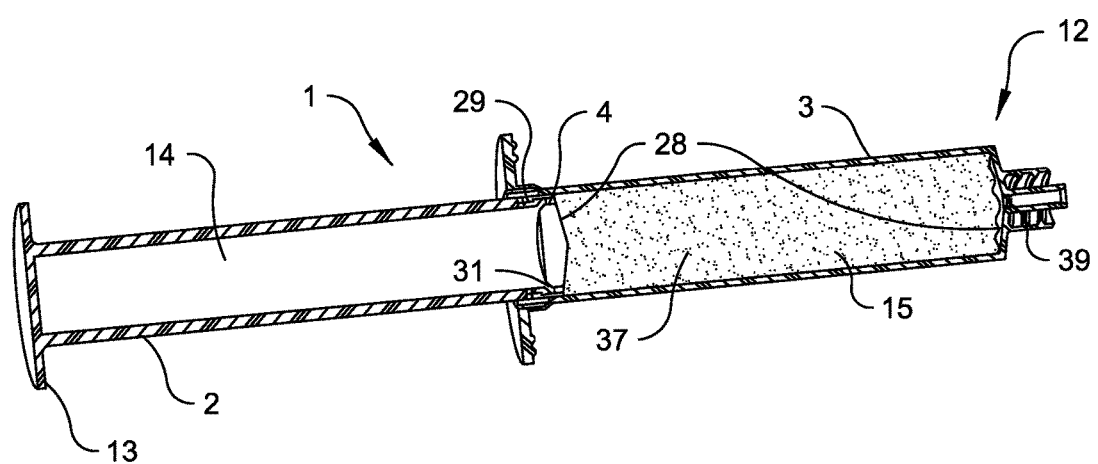
FIG. 7 is a perspective cross-sectional view illustrating a fluid within a second reservoir after transfer from a first reservoir via extension of a plunger from a barrel in accordance with an embodiment of the invention.

Referring now to FIG. 7, a syringe 1 is shown with the plunger 2 nearly fully extended from the barrel 3 and the fluid 37 originally residing within the first reservoir 14 now resides within the second reservoir 15. The valve 4 and corresponding first, second, and third sealing interfaces 28, 29, 31 remain open and the fourth sealing interface 39 remains closed until the plunger 2 is depressed from the direction of the proximate end 13 toward the distal end 12.

Figure 8:
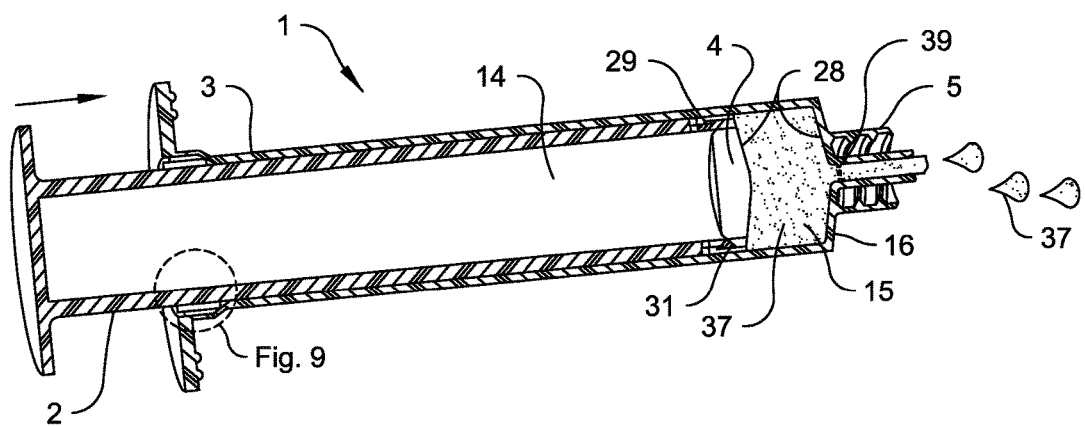
FIG. 8 is a perspective cross-sectional view illustrating ejection of a fluid from a second reservoir during retraction of a plunger into a barrel so that a valve along the plunger is closed and an optional break-away valve along the barrel is open in accordance with an embodiment of the invention.

Referring now to FIG. 8, a syringe 1 is shown nearly fully retracted so that the plunger 2 nearly completely contacts the distal wall 16 and the fluid 37 originating from the first reservoir 14 is now nearly completely ejected from the second reservoir 15. The plunger 2 is retracted by pushing the plunger 2 toward the barrel 3 along the extension axis of the syringe 1. The valve 4 and corresponding second and third sealing interfaces 29, 31 are closed to prevent the fluid 37 from reentering the first reservoir 14 and the optional fourth sealing interface 39 is open to permit the fluid 37 to traverse the nipple 5 prior to exiting the syringe 1. If the fourth sealing interface 39 is not provided, then a cap or the like (not shown) may be attached to the nipple 5 to ensure the pressure conditions required for transfer of the fluid 37 from the first reservoir 14 to the second reservoir 15. The cap is removed to permit ejection of the fluid 37 from the second reservoir 15.

Figure 9:
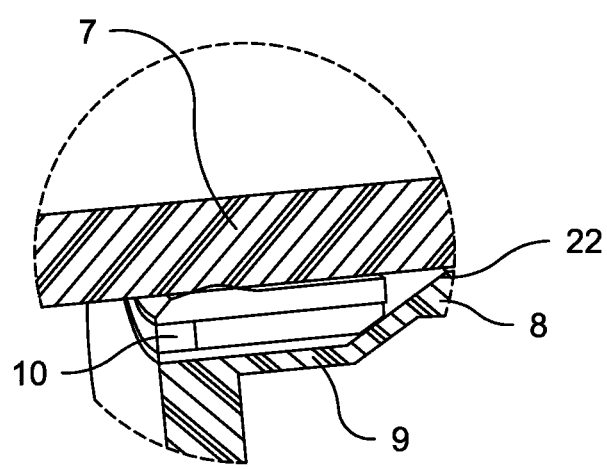
FIG. 9 is an enlarged cross-sectional view illustrating a filter element within a pocket between a plunger and a barrel whereby gas adjacent to a telescoping syringe must pass through the filter element prior to traversing a gap between the plunger and the barrel and thereafter entering a first reservoir as a fluid is transferred from a first reservoir to a second reservoir in accordance with an embodiment of the invention.
Figure 10:
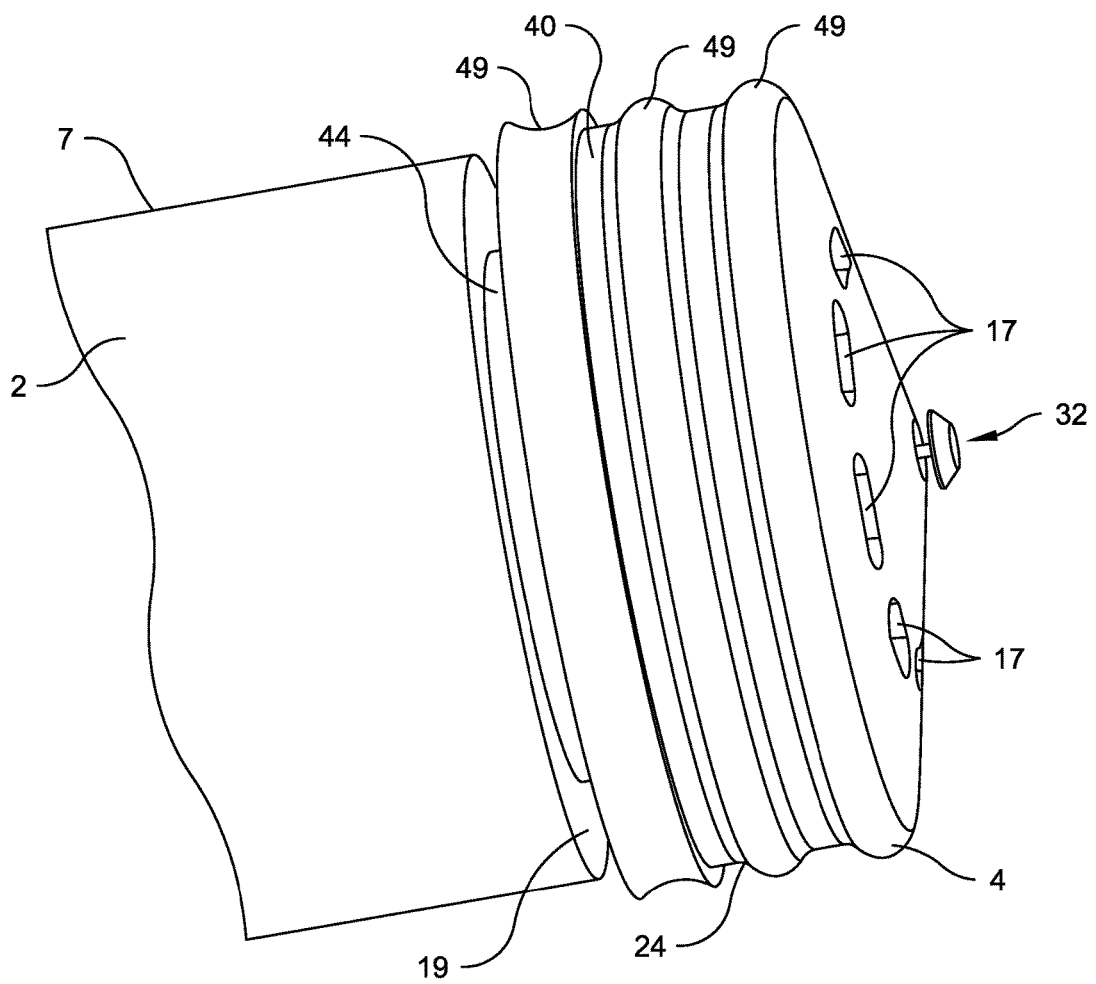
FIG. 10 is an enlarge perspective view illustrating a valve extendible from and retractable onto one end of a plunger whereby the valve is extended from the plunger, the valve includes at least one outlet (not shown), the plunger includes at least one inlet, concave and convex ridges are disposed along an outer surface of the valve, and an optional break-away valve is attached to the plunger in accordance with an embodiment of the invention.

Referring now to FIGS. 1 and 9, the syringe 1 may include an optional filter element 10 that removes particulates and other contaminants that could adversely interact or contaminate the fluid 37. In one possible embodiment, the filter element 10 could be a component, preferably annular shaped, housed within a pocket 9 disposed between the side walls 7, 8 adjacent to the gap 22. The pocket 9 may be a region whereby the gap 22 between side walls 7, 8 is larger than other portions of the same gap 22. The pocket 9 should support and secure the filter element 10 to the syringe 1, yet maintain sliding between the side walls 7, 8 and between the filter element 10 and one or both side walls 7, 8. The filter element 10 may be a mechanical filter, examples including but not limited to a charcoal-based filter or a HEPA filter.

Referring now to FIGS. 10-13, the valve 4 may include one or more ridges 49 that extend outward from the outer surface 40 along the annular extension 24. The ridges 49 may include convex or concave features which allow the valve 4 to contact the inner diameter of the barrel 3 so as to provide a slidable seal between the valve 4 and the barrel 3. The seal should be sufficient to maintain the pressure differential required between the first reservoir 14 and the second reservoir 15 to facilitate the fluid transfer described herein. Specifically, the first reservoir 14 should be at a higher pressure than the second reservoir 15 during extension of the syringe 1.

Referring again to FIGS. 11-13, the syringe 1 may include an optional biasing mechanism 48 that permits extension of the valve 4 from the plunger 2 during extension of the side wall 7 of the plunger 2 from the side wall 8 of the barrel 3 along the direction of the gap 22 and then thereafter permits retraction of the valve 4 onto the plunger 2. In some embodiments, retraction of the valve 4 by the biasing mechanism 48 may occur after some or all fluid 37 is transferred from the first reservoir 14 to the second reservoir 15. In other embodiments, retraction of the valve 4 by the biasing mechanism 48 may occur after the plunger 2 is either partially or completely extended from the barrel 3.

Referring again to FIGS. 10-14, the outer surface of the side wall 7 at the distal end 12 of the syringe 1 may include a proximal shoulder 19, an intermediate shoulder 43, and a distal shoulder 25. A first annular groove 44 is interposed between and bounded by the proximal shoulder 19 and the intermediate shoulder 43. A second annular groove 45 is interposed between and bounded by the intermediate shoulder 43 and the distal shoulder 25. The inner surface of the annular extension 24 may include an annular flange 41 and an elastic annular flange 42. A first inner annular groove 46 is interposed between and bound by the annular flange 41 and the elastic annular flange 42. A second inner annular groove 47 is interposed between and bounded by the elastic annular flange 42 and the barrier 23. The outer surface of the side wall 7 and the inner surface of the annular extension 24 are positioned so that the annular flange 41 extends into the annular groove 44, the intermediate shoulder 43 extends into the first inner annular groove 46, the elastic annular flange 42 extends into the second annular groove 45, and the distal shoulder 25 extends into the second inner annular groove 47.

Referring again to FIGS. 11-13, the annular flange 41 slides along the first annular groove 44 so as to cover the inlets 18 when the annular flange 41 is biased toward the proximal shoulder 19 and uncover the inlets 18 when the annular flange 41 is biased toward the intermediate shoulder 43. In preferred embodiments, the elastic annular flange 42 contacts the distal shoulder 25 when the annular flange 41 is biased toward the proximal shoulder 19. This arrangement requires the elastic annular flange 42 to deform as the annular flange 41 moves with the valve 4 in the direction of the intermediate shoulder 43, as represented by the shapes for the elastic annular flange 42 in FIG. 11 versus FIGS. 12 and 13. Deformation of the elastic annular flange 42 ceases when the annular flange 41 contacts the intermediate shoulder 43. The width of the first annular groove 44 should permit the annular flange 41 to move between the proximal shoulder 19 and the intermediate should 43. The width of the first inner annular groove 46 should permit the intermediate shoulder 43 to move between the annual flange 41 and the elastic annular flange 42. The width of the second inner annular groove 47 should allow the distal shoulder 25 to contact both the elastic annular flange 42 and the barrier 23.

The biasing mechanism 48 is deformable and resilient. In preferred embodiments, the elastic annular flange 42 is deformable in that it changes shape as the elastic annular flange 42 moves into and interacts with the distal shoulder 25 when the valve 4 is extended from the plunger 2 during extension of the plunger 2 from the barrel 3. The elastic annular flange 42 is resilient in that it recovers at least most of its original shape sometime after the extension of the plunger 2 from the barrel 3. The recovery process may occur with or without input by or assistance from the user. The spring-like functionality of the elastic annular flange 42 causes the valve 4 to retract onto the plunger 2 so that the annular flange 41 is once again biased toward the proximal shoulder 19 and the inlets 18 and outlets 17 are once again closed. While specific reference is made to a mechanism wherein a flange is deformable and resilient other mechanisms capable of spring or spring-like functionality are likewise applicable to embodiments of the invention.

Referring again to FIG. 11, the valve 4 is seated onto the plunger 2 before extension of the plunger 2 from the barrel 3 so that the elastic annular flange 42 contacts and interacts with the distal shoulder 25 with no or limited deformation to the elastic annular flange 42. The position of the valve 4 with respect to the plunger 2 and the barrel 3 ensures that the barrier 23 contacts the distal end 16 of the barrel 3 so that the first sealing interface 28 is closed, the annular flange 41 contacts the valve 4 and overlays the inlets 18 so that the second sealing interface 29 is closed, and the circumferential end 30 contacts the valve 4 and overlays the outlets 17 so that the third sealing interface 31 is closed.

Referring again to FIG. 12, the valve 4 is extended from the plunger 2 and the plunger 2 is equally extended from the barrel 3 so that the elastic annular flange 42 contacts and interacts with the distal shoulder 25 and the elastic annular flange 42 is deformed by the interaction. The position of the valve 4 with respect to the plunger 2 and the barrel 3 ensures that the barrier 23 contacts the distal end 16 of the barrel 3 so that the first sealing interface 28 remains closed, the annular flange 41 contacts the intermediate shoulder 43 and no longer overlays the inlets 18 so that the second sealing interface 29 is open, and the circumferential end 30 is separated from the valve 4 and no longer overlays the outlets 17 so that the third sealing interface 31 is open.

Referring again to FIG. 13, the plunger 2 is now more extended from the barrel 3 than the valve 4 is extended from the plunger 2 so that the elastic annular flange 42 remains deformed by the interaction with the distal shoulder 25. The position of the valve 4 with respect to the plunger 2 and the barrel 3 ensures that the barrier 23 no longer contacts the distal end 16 of the barrel 3 so that the first sealing interface 28 is now open, the annular flange 41 contacts the intermediate shoulder 43 and no longer overlays the inlets 18 so that the second sealing interface 29 is open, and the circumferential end 30 is separated from the valve 4 and no longer overlays the outlets 17 so that the third sealing interface 31 is open. A portion of the fluid 37 from the first reservoir 14 now resides within the second reservoir 15.

Figure 11:
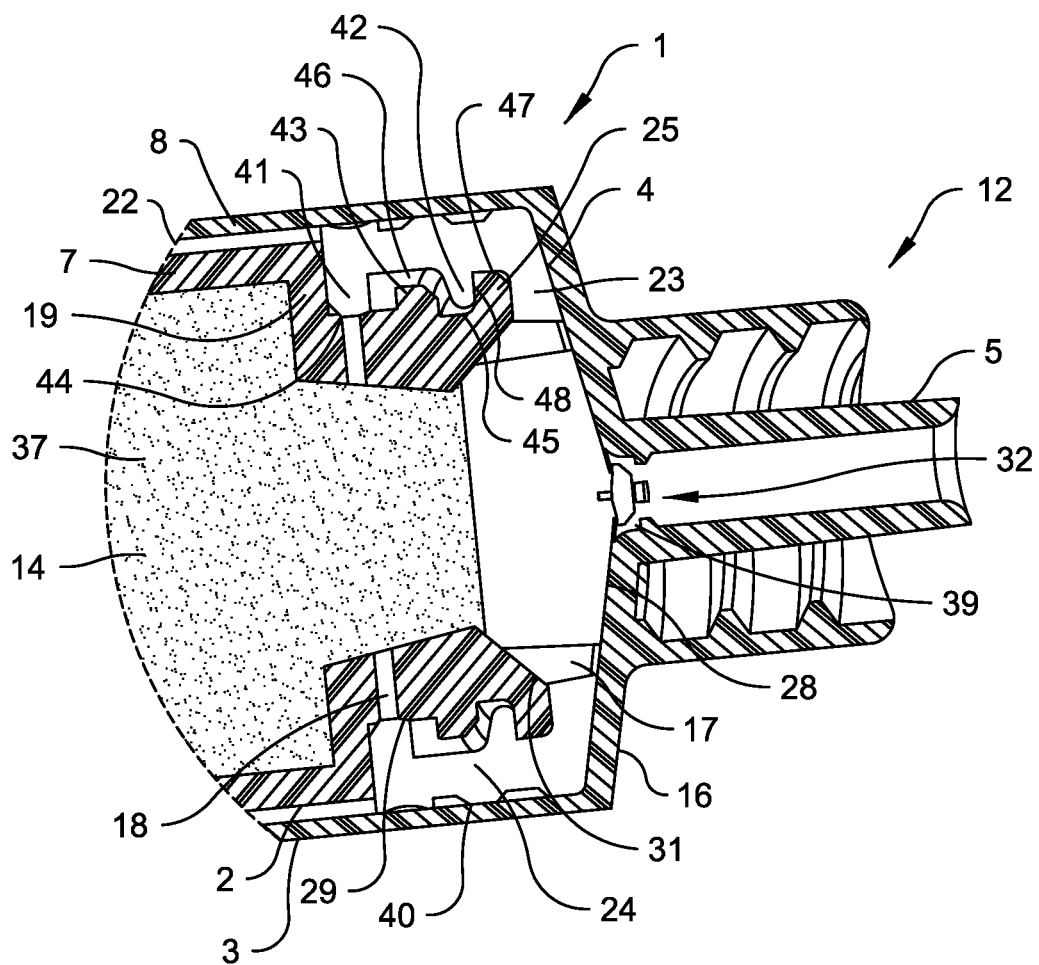
FIG. 11 is an enlarged cross-sectional view illustrating a valve with a biasing mechanism prior to extension of a plunger from a barrel whereby the valve is disposed in a closed configuration to prevent escape of a fluid from a first reservoir within the plunger in accordance with an embodiment of the invention.

The mechanical energy stored in the valve 4 due to deformation of the elastic annular flange 42 permits the elastic annular flange 42 to recover at least most of its original shape so that the valve 4 returns to its original position relative to the plunger 2 such as in FIG. 11. When this event occurs, however, it is often preferred that at least a majority of the fluid 37 from the first reservoir 14 now resides within the second reservoir 15.

Figure 12:
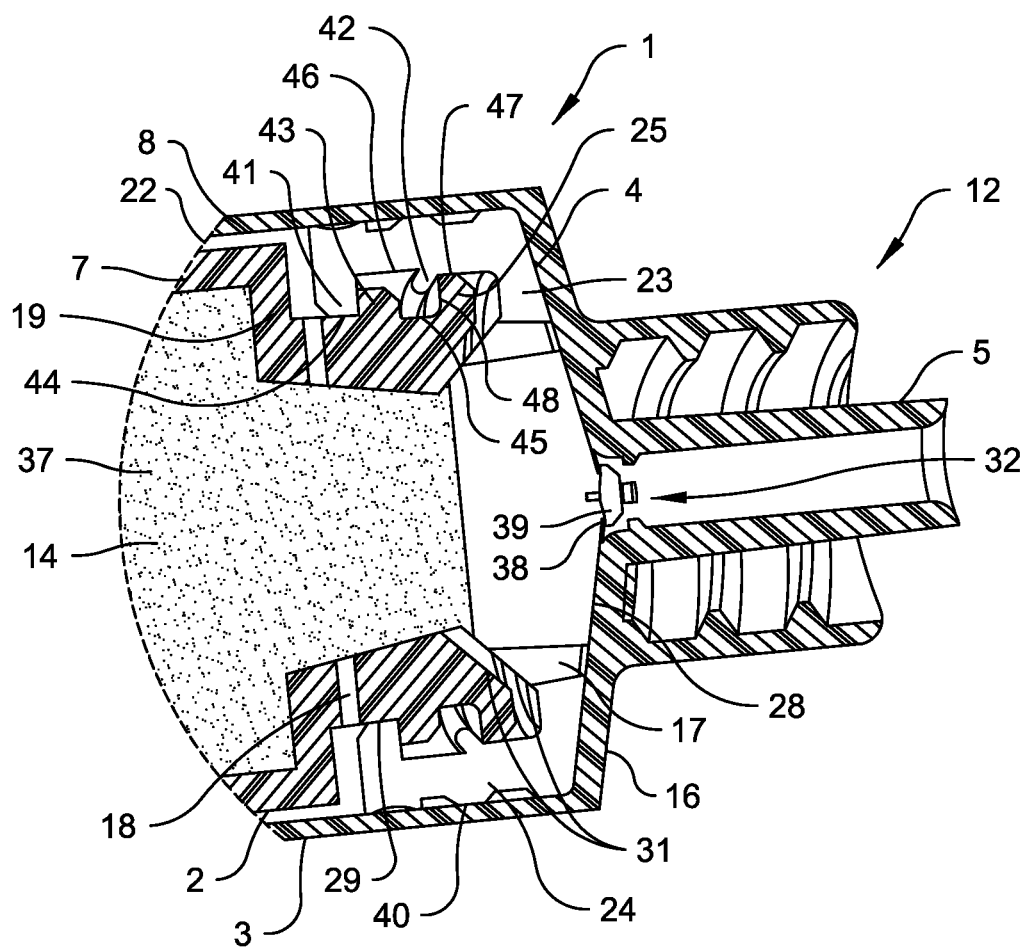
FIG. 12 is an enlarged cross-sectional view illustrating a valve with a biasing mechanism after initial extension of a plunger from a barrel whereby the valve is disposed in an open configuration to permit gas to enter a first reservoir and to permit transfer of a fluid from the first reservoir within the plunger to a second reservoir within the barrel in accordance with an embodiment of the invention.
Figure 13:
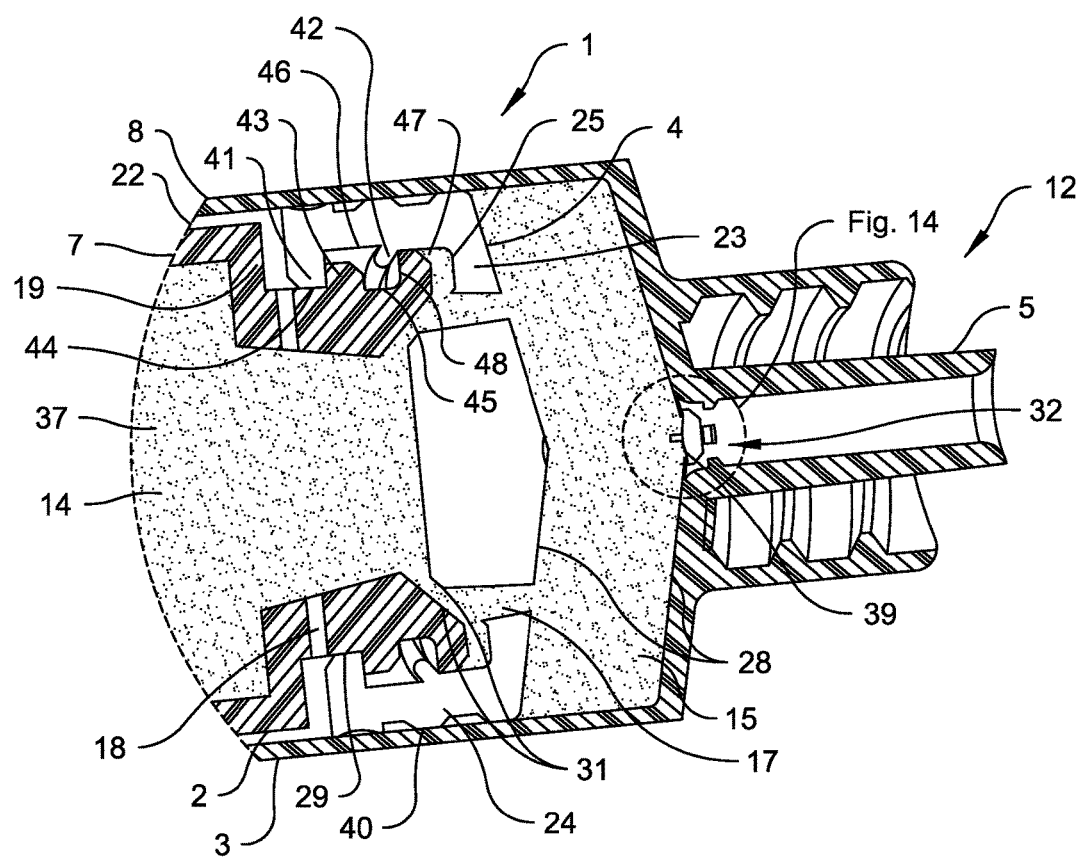
FIG. 13 is an enlarged cross-sectional view illustrating a valve with a biasing mechanism during extension of a plunger from a barrel whereby the valve is disposed in an open configuration permitting transfer of a fluid from a first reservoir within the plunger to a second reservoir within the barrel and further permitting replacement of fluid exiting the first reservoir by gas drawn into the syringe during extension in accordance with an embodiment of the invention.
Figure 14A:
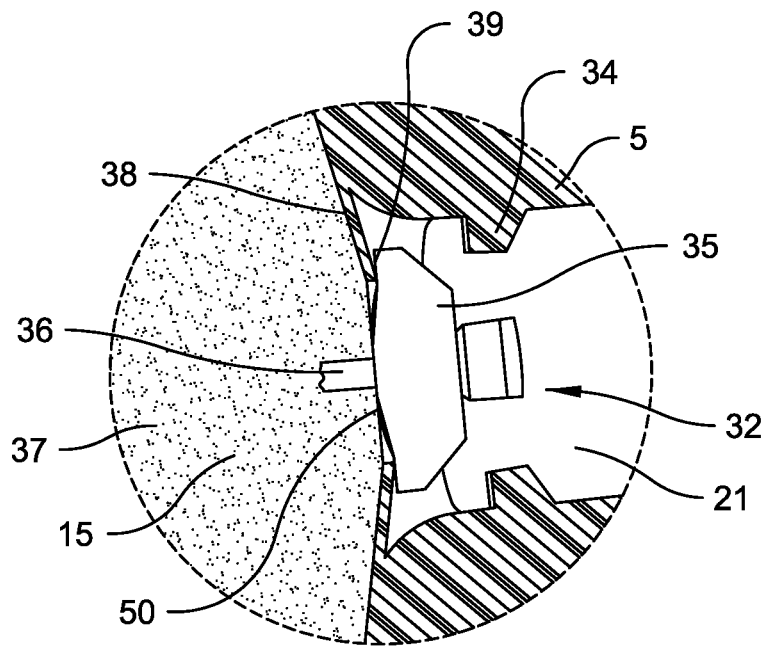
FIG. 14a is an enlarged cross-sectional view illustrating a break-away valve after separation from a one-way fluid/gas transfer valve and prior to retraction of a plunger into a barrel whereby a plug within the break-away valve provides a seal that prevents gas from entering the syringe via a nipple in accordance with an embodiment of the invention.

Referring now to FIGS. 12, 13 and 14a, a fourth sealing interface 39 may be provided by a break-away valve 32 and a diaphragm 38 facilitating ejection of fluid 37 from the syringe 1 when the fourth sealing interface 39 is open and preventing or limiting ejection of fluid 37 from the syringe 1 when the fourth sealing interface 39 is closed. The diaphragm 38 may be attached to the barrel 3 adjacent to the intersection between barrel 3 and the nipple 5. The fourth sealing interface 39 may be closed when a plug 32 and a stem 36 are attached to or separated from the valve 4, the former represented in FIGS. 12 and 13 and the latter represented in FIG. 14a, so that the stem 36 resides within an opening 50 through the diaphragm 38 and the plug 32 physically contacts the diaphragm 38. The fourth sealing interface 39 is closed during extension of the plunger 2 from the barrel 3 to prevent ejection of fluid 37 from the second reservoir 15.

Figure 14B:
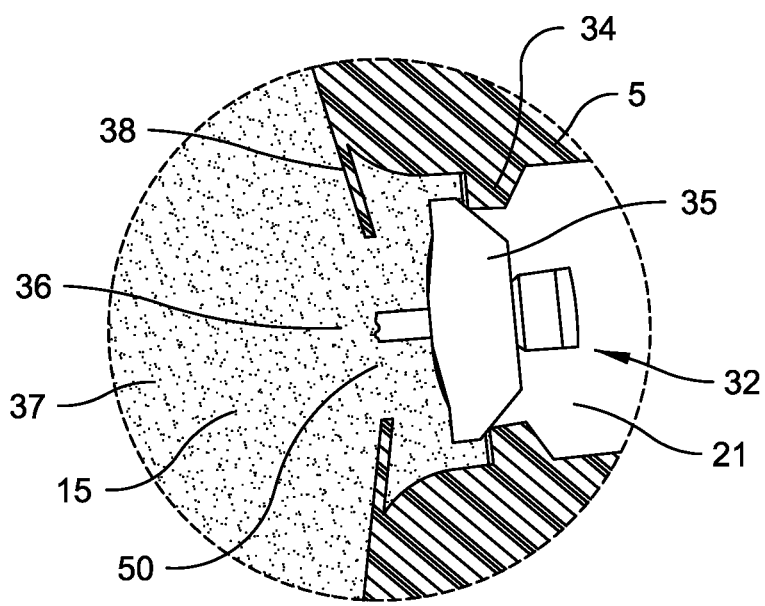
FIG. 14b is an enlarged cross-sectional view illustrating a break-away valve after separation from a one-way fluid/gas transfer valve and during retraction of a plunger into a barrel whereby a plug within the break-away valve is positioned within a nipple to facilitate ejection of a fluid from a syringe via the nipple in accordance with an embodiment of the invention.

Referring now to FIGS. 12, 13 and 14b, the fourth sealing interface 39 is open during retraction of the plunger 2 into the barrel 3 causing fluid 37 to flow out of the second reservoir 15 into and through the nipple 5. The resultant flow field unseats the plug 35 and the stem 36 from the diaphragm 38 causing both to move into the nipple 5. In many applications, it may be undesirable for the plug 35 and the stem 36 to remain contained within the syringe 1. One or more mechanical stops 34 may be provided along the inside surface of the nipple 5 adjacent to the diaphragm 38 in order to arrest the plug 35 and the stem 36 within the nipple 5. The opening 50 along the diaphragm 38 and the interaction between the plug 35 and the stop(s) 34 should allow the desired flow rate(s) of fluid 37 from the syringe 1.

As is evident from the explanation herein, the described invention is a telescoping syringe which may be applicable to storing and dispensing a variety of fluids including, but not limited to, medications, adhesives, solvents, and cleaners.

The description above indicates that a great degree of flexibility is offered in terms of the present invention. Although various embodiments have been described in considerable detail with reference to certain preferred versions thereof, other versions are possible. Therefore, the spirit and scope of the appended claims should not be limited to the description of the preferred versions contained herein.

What is claimed is:

1. A telescoping syringe comprising:
  (a) a barrel;
  (b) a plunger extendible from and retractable into said barrel, said plunger defining a first reservoir, said barrel defining a second reservoir as said plunger is extended from said barrel; and
  (c) a one-way valve disposed at one end of said plunger adjacent to a nipple extending from said barrel, a first sealing interface provided by said one-way valve and a distal wall along said barrel adjacent to said nipple, a second sealing interface provided by an annular flange along said one-way valve and an annular groove along said plunger, a third sealing interface provided by said one-way valve and a circumferential end of said plunger;
  wherein:
    said first sealing interface, said second sealing interface, and said third sealing interface are closed prior to extension of said plunger from said barrel thereby preventing a gas from entering and a fluid from exiting said first reservoir;
    said first sealing interface, said second sealing interface, and said third sealing interface are open when said plunger is extended from said barrel so that said gas enters said first reservoir via at least one inlet along said annular groove and said fluid is communicated into said second reservoir via at least one outlet along said one-way valve;
    said second sealing interface and said third sealing interface are closed when said plunger is retracted into said barrel thereby allowing said fluid to exit said second reservoir via said nipple.

2. The telescoping syringe of claim 1, wherein said first sealing interface is closed when said one-way valve contacts said distal wall and said first sealing interface is open when said one-way valve is separated from said distal wall.

3. The telescoping syringe of claim 1, wherein said annular flange slidingly engages said annular groove, said second sealing interface is closed when said annular flange completely covers said at least one inlet along said annular groove and said second sealing interface is open when said annular flange does not completely cover said at least one inlet.

4. The telescoping syringe of claim 3, wherein said second sealing interface extends along and includes a proximal shoulder along said plunger and an annular extension along said one-way valve to the extent which contact is permitted between said proximal shoulder and said annular extension, said second sealing interface is closed when said annular extension contacts said proximal shoulder and open when said annular extension is pulled away from and no longer contacts said proximal shoulder.

5. The telescoping syringe of claim 1, wherein said third sealing interface is closed when said circumferential end contacts said one-way valve so as to overlay and cover said at least one outlet along said one-way valve and said third sealing interface is open when said circumferential end is separated from said one-way valve.

6. The telescoping syringe of claim 1, further comprising:
   (d) a break-away valve that engages said barrel adjacent to said nipple thereby defining a fourth sealing interface;
   wherein:
      said break-away valve is attached to said one-way valve and said fourth sealing interface is closed prior to extension of said plunger from said barrel thereby preventing said gas from entering said barrel;
      said break-away valve is detached from said one-way valve and said fourth sealing interface is closed during extension of said plunger from said barrel thereby forming a lower pressure within said second reservoir which facilitates transfer of said fluid from said first reservoir to said second reservoir;
      said break-away valve is detached from said one-way valve and said fourth sealing interface is open during retraction of said plunger into said barrel thereby allowing said fluid to exit said second reservoir via said nipple.

7. The telescoping syringe of claim 6, wherein said break-away valve includes a stem interposed between said one-way valve and a plug, said plug attached to said one-way valve via said stem, said stem permits said plug to detach from said one-way valve when said plunger is extended from said barrel.

8. The telescoping syringe of claim 7, further comprising:
   (e) a diaphragm adjacent to said nipple, said diaphragm interposed between said plug and said one-way valve.

9. The telescoping syringe of claim 8, wherein said stem traverses an opening through said diaphragm, said stem is attached to said one-way valve and said plug before extension of said plunger from said barrel.

10. The telescoping syringe of claim 8, wherein said fourth sealing interface is closed when said plug contacts said diaphragm and said fourth sealing interface is open when said plug is separated from said diaphragm.

11. The telescoping syringe of claim 7, further comprising:
   (e) at least one stop disposed along an opening through said nipple, said at least one stop permits said fluid to traverse and exit said nipple and prevents said plug from exiting said nipple.

12. The telescoping syringe of claim 1, further comprising:
   (d) a filter element disposed along said telescoping syringe, said gas passes through said filter element prior to entering said at least one inlet.

13. The telescoping syringe of claim 12, wherein said filter element is interposed between a first side wall of said plunger and a second side wall of said barrel, said gas traverses a gap between said first side wall and said second side wall.

14. The telescoping syringe of claim 12, wherein said filter element is a HEPA filter.

15. The telescoping syringe of claim 1, further comprising:
   (d) a biasing mechanism which permits said one-way valve to extend from said plunger when extended from said barrel and then causes said one-way valve to retract onto said plunger.

16. The telescoping syringe of claim 15, wherein said biasing mechanism causes said one-way valve to retract onto said plunger after at least some of said fluid is transferred from said first reservoir to said second reservoir.

17. The telescoping syringe of claim 15, wherein said biasing mechanism causes said one-way valve to retract onto said plunger after said plunger extends from said barrel.

18. The telescoping syringe of claim 15, said biasing mechanism is deformable and resilient.

19. The telescoping syringe of claim 15, said biasing mechanism includes an elastic annular flange along said one-way valve which interacts with a shoulder along said plunger.

* * * * *